(12) United States Patent
Yousef et al.

(10) Patent No.: US 12,329,729 B1
(45) Date of Patent: Jun. 17, 2025

(54) METHOD OF TREATING CANCER IN A SUBJECT

(71) Applicant: IMAM MOHAMMAD IBN SAUD ISLAMIC UNIVERSITY, Riyadh (SA)

(72) Inventors: Tarek Ahmed Yousef, Riyadh (SA); Saad Shaaban, Almansourah (EG); Ahmed A. Al-Karmalawy, Riyadh (SA); Ayman Abo Elmaaty, Riyadh (SA)

(73) Assignee: IMAM MOHAMMAD IBN SAUD ISLAMIC UNIVERSITY, Riyadh (SA)

( * ) Notice: Subject to any disclaimer, the term of this patent is extended or adjusted under 35 U.S.C. 154(b) by 0 days.

(21) Appl. No.: 18/895,223

(22) Filed: Sep. 24, 2024

(51) Int. Cl.
  *A61K 31/15* (2006.01)
  *A61P 35/00* (2006.01)
  *C07C 391/02* (2006.01)

(52) U.S. Cl.
  CPC ............ *A61K 31/15* (2013.01); *A61P 35/00* (2018.01); *C07C 391/02* (2013.01)

(58) Field of Classification Search
  CPC ........ A61P 35/00; A61K 31/15; C07C 391/02
  See application file for complete search history.

(56) References Cited

U.S. PATENT DOCUMENTS

| | | |
|---|---|---|
| 11,814,346 B1 | 11/2023 | Shabaan et al. |
| 11,969,442 B1 | 4/2024 | Ahmed et al. |
| 11,976,033 B1 | 5/2024 | Ahmed et al. |

FOREIGN PATENT DOCUMENTS

WO   2022/076611 A1   4/2022

OTHER PUBLICATIONS

Sara Lorenzoni, et al., "Organoselenium compounds as functionalizing agents for gold nanoparticles in cancer therapy", Colloids and Surfaces B: Biointerfaces, vol. 219, Nov. 2022, 112828, 5 pages.

*Primary Examiner* — Amanda L. Aguirre
*Assistant Examiner* — Chris E Simmons
(74) *Attorney, Agent, or Firm* — Oblon, McClelland, Maier & Neustadt, L.L.P.

(57) ABSTRACT

A method of treating cancer in a subject in need thereof including administering to the subject a therapeutically effective amount of the compound of formula (I) or a pharmaceutically acceptable salt thereof,

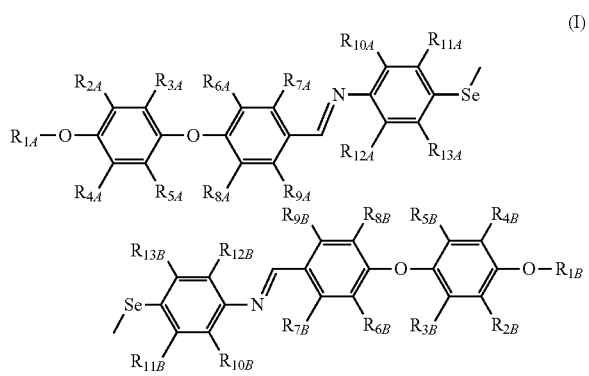

where each of $R_{1A}$-$R_{13A}$ and $R_{1B}$-$R_{13B}$ is independently selected from the group consisting of a hydrogen atom, a halogen atom, a nitro group, a cyano group, a hydroxyl group, an alkoxy group, an optionally substituted alkyl group, an optionally substituted cycloalkyl group, an optionally substituted arylalkyl group, and an optionally substituted aryl group.

11 Claims, 1 Drawing Sheet

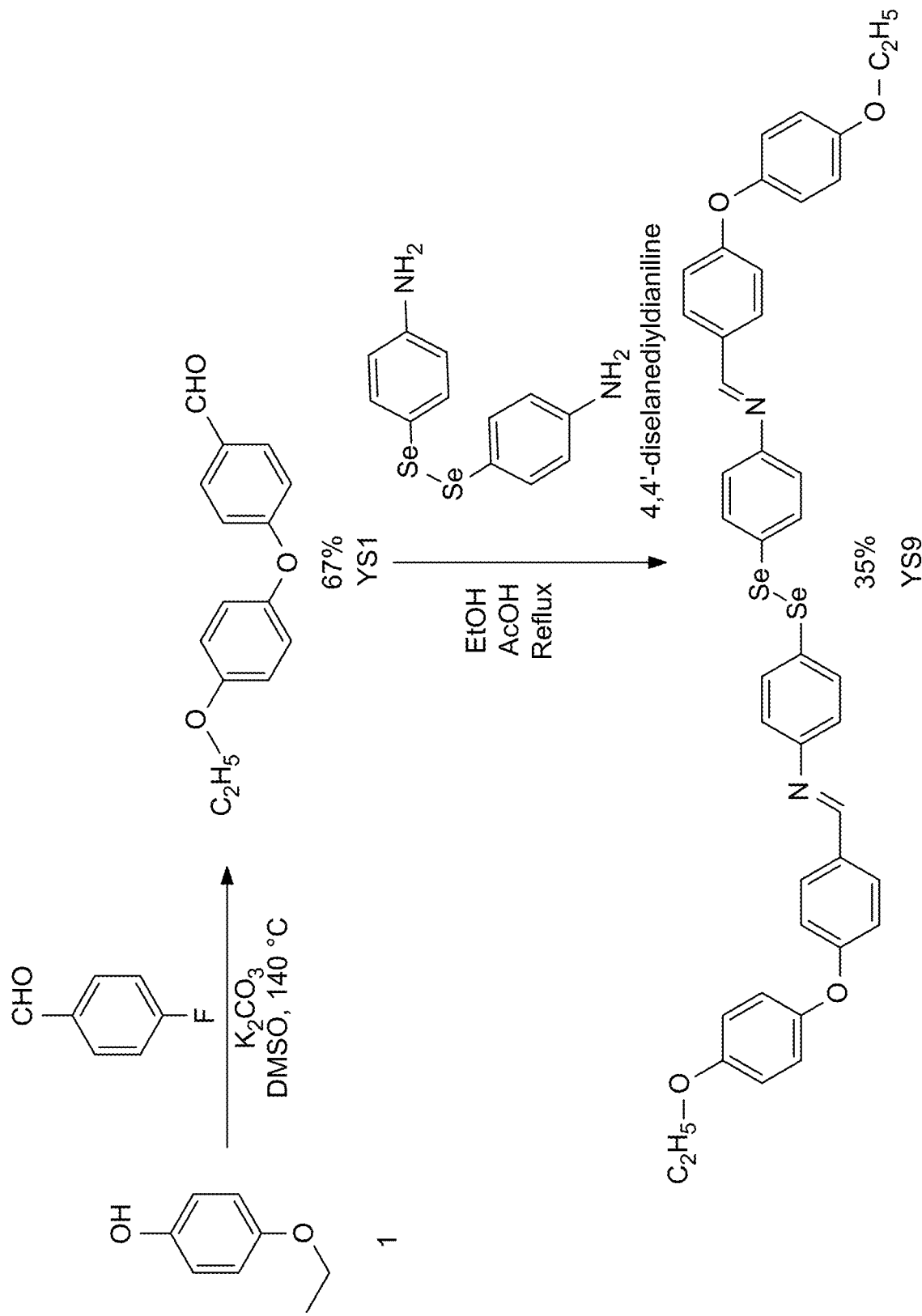

METHOD OF TREATING CANCER IN A SUBJECT

BACKGROUND

Technical Field

The present disclosure is directed towards a pharmaceutical composition and method for cancer treatment, and more particularly, directed towards a method of treating cancer in a subject in need thereof.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Cancer is a leading cause of death globally and presents a major obstacle to human survival worldwide. Cancer is marked by the uncontrolled proliferation and dissemination of abnormal cells. The onset of cancer occurs when cells undergo genetic mutations that disrupt their normal processes of growth, division, and programmed cell death. Researchers estimate that carcinoma, which is the most common type of epithelial tissue cancer, accounts for nearly 72% of all formally recorded cancer deaths worldwide, with projections indicating a rise to 75% in the coming years. Other prominent cancer types encompass colorectal cancer, breast cancer, prostate cancer, lung cancer, and leukemia. A plurality of therapies are frequently administered to combat the persistent and ongoing progress of cancerous cells, thereby extending their duration and improving the quality of life of individuals with carcinoma. However, most chemotherapeutic medications negatively affect healthy cells and may cause serious side effects, especially when administered in high doses. Apoptosis, also known as programmed cell death or cellular suicide, is a vital biological mechanism responsible for eliminating damaged, aged, or unnecessary cells. Key components in the apoptosis process include caspases, which are protease enzymes pivotal in initiating and executing apoptosis by cleaving specific cellular proteins. In addition, the Bcl-2 family governs the intrinsic pathway by regulating mitochondrial membrane permeability. Some members of the Bcl-2 family promote apoptosis (pro-apoptotic), while others inhibit it (anti-apoptotic). Insights into apoptosis have shed light on the development of cancer therapies that induce apoptosis in malignant cells. Moreover, cancer and inflammation are completely connected, and various inflammatory markers (e.g., reactive oxygen species (ROS), C-reactive protein (CRP), tumor necrosis factors (TNF), and interleukins (ILs)) are often implicated in cancer development and progression. Hence, manipulating these inflammatory markers can offer valuable insights into certain cancers' risk, progression, and treatment response. However, current anti-cancer therapies are toxic in nature and economically taxing. Therefore, a need arises for a better, safer, and economically favorable anti-cancer therapy.

Hence, it is one object of the present disclosure to provide a method of treating cancer in a subject in need of it that may circumvent the above-stated drawbacks, such as low efficiency, adverse drug side effects, and the expensive nature of present methods and publications.

SUMMARY

In an exemplary embodiment, a method of treating cancer in a subject in need thereof is described. The method includes administering to the subject a therapeutically effective amount of the compound of formula (I) or a pharmaceutically acceptable salt thereof:

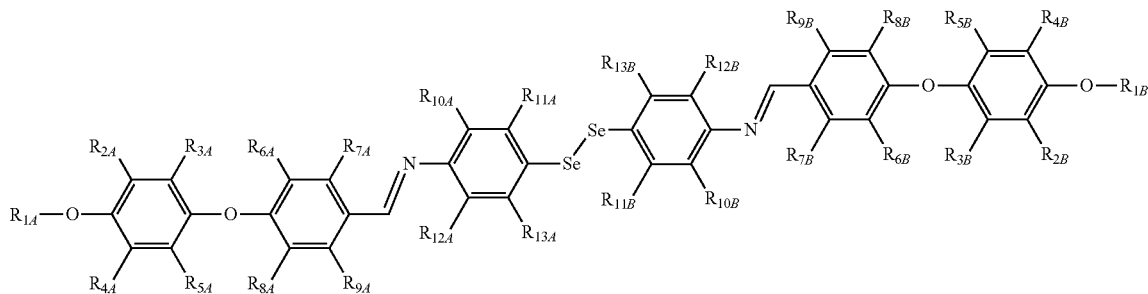

(I), where each of $R_{1A}$-$R_{13A}$ and $R_{1B}$-$R_{13B}$ is independently selected from the group consisting of a hydrogen atom, a halogen atom, a nitro group, a cyano group, a hydroxyl group, an alkoxy group, an optionally substituted alkyl group, an optionally substituted cycloalkyl group, an optionally substituted arylalkyl group, and an optionally substituted aryl group.

In some embodiments, the compound of formula (I) is compound (II) or a pharmaceutically acceptable salt thereof:

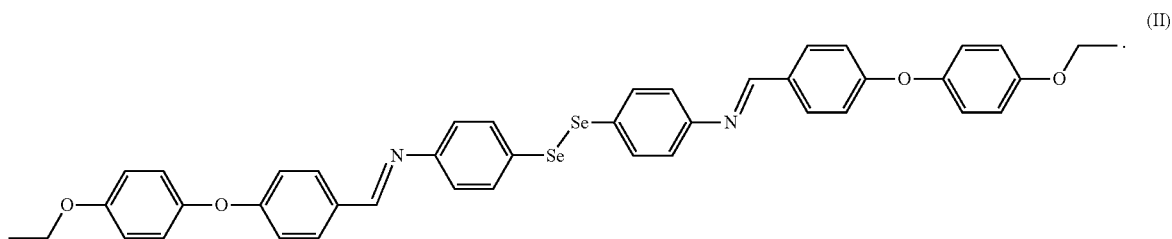 [SMILES: CCOc1ccc(Oc2ccc(/C=N/c3ccc([Se][Se]c4ccc(/N=C/c5ccc(Oc6ccc(OCC)cc6)cc5)cc4)cc3)cc2)cc1]

In some embodiments, the cancer is at least one selected from the group consisting of non-small cell lung cancer, colorectal carcinoma, prostate cancer, pharynx squamous carcinoma, triple-negative breast cancer, and cervical cancer.

In some embodiments, the cancer is non-small cell lung cancer.

In some embodiments, the compound of formula (I) or a pharmaceutically acceptable salt thereof induces apoptosis by upregulating at least one gene selected from the group consisting of p53, BAX, Caspase 3, Caspase 6, Caspase 8, and Caspase 9.

In some embodiments, the compound of formula (I) or a pharmaceutically acceptable salt thereof induces apoptosis by downregulating at least one gene selected from the group consisting of BCL-2, MMP2, and MMP9.

In some embodiments, the compound of formula (I) or a pharmaceutically acceptable salt thereof acts to downregulate at least one anti-inflammatory marker gene selected from the group consisting of COX-2, IL-6, and IL-1β.

In some embodiments, the method of administering to the subject is oral administration, parenteral administration, rectal administration, topical administration, transdermal administration, intralesional administration, or inhalation administration.

In some embodiments, the therapeutically effective amount of the compound of formula (I) or a pharmaceutically acceptable salt thereof is from 0.1 milligrams per kilogram (mg/kg) to 1000 mg/kg.

In some embodiments, the compound of formula (I) or a pharmaceutically acceptable salt thereof is administered as a pharmaceutical composition comprising the compound of formula (I) or a pharmaceutically acceptable salt thereof and a pharmaceutically acceptable carrier and/or excipient.

In some embodiments, the pharmaceutically acceptable carrier and/or excipient is at least one selected from the group consisting of a buffer, an inorganic salt, a synthetic fatty acid, a vegetable oil, a fatty ester, a surfactant, and a polymer.

In some embodiments, the pharmaceutical composition further includes one or more of a sweetener, a flavoring, and a colorant.

In another exemplary embodiment, a pharmaceutical composition is described. The pharmaceutical composition includes a compound of formula (I) or a pharmaceutically acceptable salt thereof and a pharmaceutically acceptable carrier and/or excipient:

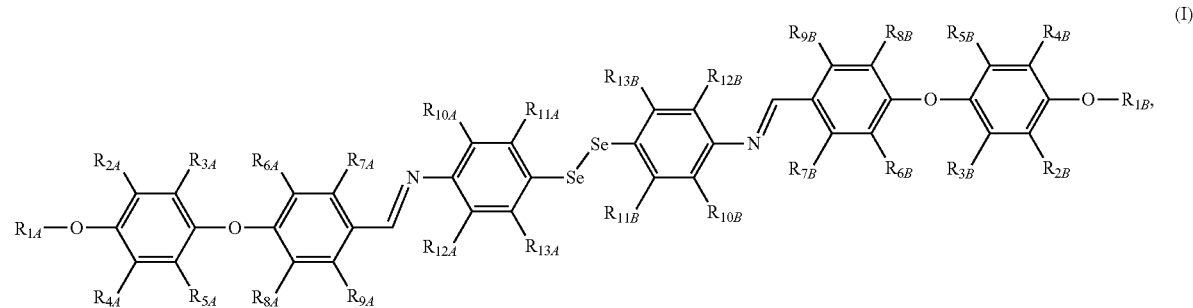

where each of $R_{1A}$-$R_{13A}$ and $R_{1B}$-$R_{13B}$ is independently selected from the group consisting of a hydrogen atom, a halogen atom, a nitro group, a cyano group, a hydroxyl group, an alkoxy group, an optionally substituted alkyl group, an optionally substituted cycloalkyl group, an optionally substituted arylalkyl group, and an optionally substituted aryl group.

In some embodiments, the compound of formula (I) is compound (II) or a pharmaceutically acceptable salt thereof:

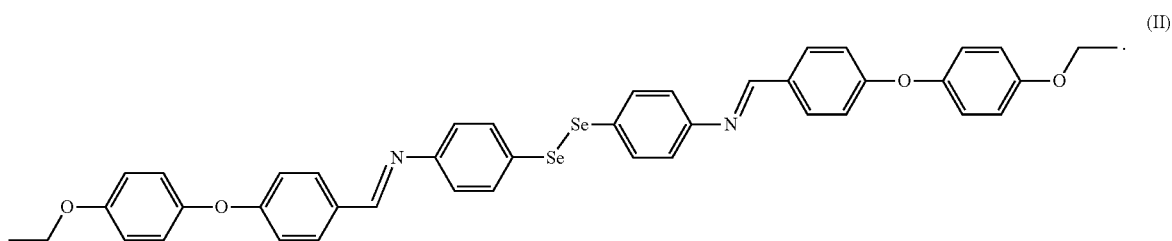 [SMILES: CCOc1ccc(Oc2ccc(/C=N/c3ccc([Se][Se]c4ccc(/N=C/c5ccc(Oc6ccc(OCC)cc6)cc5)cc4)cc3)cc2)cc1]

(II)

In some embodiments, the pharmaceutically acceptable carrier and/or excipient is at least one selected from the group consisting of a buffer, an inorganic salt, a synthetic fatty acid, a vegetable oil, a fatty ester, a surfactant, and a polymer.

In some embodiments, the pharmaceutical composition further includes one or more of a sweetener, a flavoring, and a colorant.

In some embodiments, the composition is formulated for at least one mode of administration selected from the group consisting of oral administration, parenteral administration, rectal administration, topical administration, transdermal administration, intralesional administration, and inhalation administration.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawing, wherein:

The drawing is a schematic illustration depicting the synthesis of YS1 and YS9 chemical compounds, according to certain embodiments.

DETAILED DESCRIPTION

As used herein, the words "a," "an," and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the term 'cancer' refers to all types of cancer, neoplasm, or malignant tumors found in mammals (e.g., humans), including leukemias, lymphomas, carcinomas, and sarcomas. Exemplary cancers that may be treated with the method or composition provided herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with the method provided herein include cancer of the thyroid, endocrine system, brain, breast, cervix, colon, head and neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulinoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term 'half maximal inhibitory concentration ($IC_{50}$)' refers to the measure of the potency of a substance in inhibiting a specific biological or biochemical function. $IC_{50}$ is a quantitative measure that indicates how much of a particular inhibitory substance (e.g., drug) is needed to inhibit, in vitro, a given biological process or biological component by 50%. The biological component can be an enzyme, cell, cell receptor, or microorganism. $IC_{50}$ values are typically expressed as molar concentration.

As used herein, "analogue" refers to a chemical compound structurally similar to a parent compound, but differs slightly in composition (e.g., one atom or functional group is different, added, or removed). The analogue may or may not have chemical or physical properties different from the original compound and may or may not have improved biological and/or chemical activity. For example, the analogue may be more hydrophilic or have altered reactivity compared to the parent compound. The analogue may mimic the chemical and/or biological activity of the parent compound (i.e., it may have similar or identical activity), or, in some cases, may have increased or decreased activity. The analogue may be a naturally or non-naturally occurring variant of the original compound. Other types of analogues include isomers (enantiomers, diastereomers, and the like) and other types of chiral variants of a compound, as well as structural isomers.

As used herein, "derivative" refers to a chemically or biologically modified version of a chemical compound structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or have altered reactivity compared to the parent compound. Derivatization (i.e., modification) may involve the substitution of one or more moieties within the molecule (e.g., a change in a functional group). The term "derivative" also includes conjugates and prodrugs of a parent compound (i.e., chemically modified derivatives that can be converted into the original compound under physiological conditions).

The term "therapeutically effective amount," as used herein, refers to the amount of the complex being administered, which will relieve to some extent one or more of the symptoms of the disorder being treated. In reference to cancer or pathologies related to increased cell division, a therapeutically effective amount refers to that amount which has the effect of at least one of the following: (1) reducing the size of a tumor, (2) inhibiting (that is, slowing to some extent, preferably stopping) aberrant cell division, growth or proliferation, for example, cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer and (5) inducing apoptosis of cancer cells or tumor cells.

As used herein, the terms "therapies" and "therapy" can refer to any method(s), composition(s), and/or agent(s), and/or complexes that can be used in the prevention, treatment and/or management of cancer or one or more symptoms thereof.

As used herein, the terms "treat," "treatment," and "treating" in the context of the administration of a therapy to a subject in need thereof refer to the reduction or inhibition of the progression and or duration of cancer, the reduction or amelioration of the severity of cancer, and/or the amelioration of one or more symptoms thereof resulting from the administration of one or more therapies. In some embodiments, the subject is a mammal. In some embodiments, mammals may include mice, rats, rabbits, dogs, cats, primates (such as monkeys and apes), and humans. In one embodiment, the subject is a human. "Treating" or "treatment" of a disease includes preventing the disease from occurring in a subject that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms mean that the life expectancy of an individual affected with cancer will be increased or that one or more of the symptoms of the disease will be reduced. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, and (12) an increase in the number of patients in remission. In certain embodiments, such terms refer to stabilizing or reducing the cancer stem cell population. In some embodiments, such terms refer to a stabilization or reduction in the growth of cancer cells. In some embodiments, such terms refer to stabilization or reduction in the cancer stem cell population and a reduction in the cancer cell population. In some embodiments, such terms refer to a stabilization or reduction in the growth and or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in the survival rate of a patient population. In further embodiments, such terms refer to an increase in the response rate, the durability of response, or the number of patients who respond or are in remission. In some embodiments, such terms refer to a decrease in the hospitalization rate of a patient population and/or a decrease in hospitalization length for a patient population.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer. White women or a person with (i) certain inherited genes (e.g., mutated BRCA1, BRCA2, ATM, TP53, CHEK2, PTEN, CDH1, STK11, and PALB2), (ii) radiation occurred to one's chest, and/or (iii) exposure to diethylstilbestrol (DES) are at a higher risk of contracting breast cancer. People who (i) smoke or regularly breathe in second-hand smoke, (ii) exposed to carcinogens including, but not limited to polycyclic aromatic hydrocarbons (e. g. benzo[a]pyrene, benz[a]anthracene, and methylated derivatives thereof), asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer.

A "pharmaceutical composition" refers to a mixture of the compounds described herein or pharmaceutically acceptable salts, esters, or prodrugs thereof, with other chemical components, such as physiologically acceptable carriers and excipients.

"Pharmaceutically acceptable salt" or "pharmaceutically acceptable ester" refers to a compound in a pharmaceutically acceptable form such as an ester, a phosphate ester, a salt of an ester, or a related) which, upon administration to a subject in need thereof, provides the compound of Formula (I) deserved herein. Pharmaceutically acceptable salts and esters retain the biological effectiveness and properties of the free bases, which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Suitable salts include those derived from alkali metals such as potassium and sodium, and alkaline earth metals such as calcium and magnesium, among numerous other acids well-known in the art.

As used herein, a "pharmaceutically acceptable carrier" refers to a carrier or diluent that does not cause significant irritation to an organism and does not abrogate the biological activity and properties of the compound of Formula (I). The term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

An "excipient" refers to an inert substance added to a pharmaceutical composition to facilitate further administration of a compound. Examples, without limitation, of excipients include calcium carbonate, calcium phosphate, various sugars and types of starch, cellulose derivatives, gelatin, vegetable oils, and polyethylene glycols.

As used herein, the term "aryl", as used herein, and unless otherwise specified, refers to a substituent that is derived from an aromatic hydrocarbon (arene) that has had a hydrogen atom removed from a ring carbon atom. Aryl includes phenyl, biphenyl, naphthyl, anthracenyl, and the like.

The term "alkyl," by itself or as part of another substituent, means, unless otherwise stated, a straight (i.e., unbranched) or branched carbon chain (or carbon), or a combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs, and isomers of, for example, n-pentyl, n-hexyl, n-heptyl, n-octyl, and the like. An unsaturated alkyl group has one or more double or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "cycloalkyl" refers to any univalent radical derived from a cycloalkane by the removal of an atom of hydrogen having C1-C10 carbon atoms.

As used herein, the term "alkoxy" refers to an alkyl group that is singularly bonded to oxygen; thus, R—O, where R has C1-C10 carbon atoms.

As used herein, the term 'hydroxyl group' refers to the functional group with the chemical formula —OH— composed of one oxygen atom covalently bonded to one hydrogen atom.

As used herein, the term 'halogen atom' refers to the atom of the group in the periodic table consisting of six chemically related elements: fluorine (F), chlorine (Cl), bromine (Br), or iodine (I).

As used herein, the term 'nitro group' refers to the chemical functional group composed of one nitrogen atom (N) and two oxygen atoms (O) bonded together. It is represented by the chemical formula —$NO_2$. Nitro groups are known for their strong electron-withdrawing properties, making molecules containing them highly reactive.

As used herein, the term 'cyano group' is the chemical functional group consisting of a carbon atom (C) triple-bonded to a nitrogen atom (N), with the formula —CN. It is denoted as "CN" in chemical structures.

As used herein, the term "substituted" refers to at least one hydrogen atom that is replaced with a non-hydrogen group, provided that normal valencies are maintained and that the substitution results in a stable compound. When a group is noted as "optionally substituted", the group may or may not contain non-hydrogen substituents. When present, the substituent(s) may be selected from alkyl, halo (e.g., chloro, bromo, iodo, fluoro), hydroxyl, alkoxy, oxo, alkanoyl, aryloxy, alkanoyloxy, amino (—$NH_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkylsulfonyl, arylsulfonyl, arylalkylsulfonyl, sulfonamide (e.g., —$SO_2NH_2$), substituted sulfonamide (e.g., —$SO_2$NHalkyl, —$SO_2$NHaryl, —$SO_2$NHarylalkyl, or cases where there are two substituents on one nitrogen selected from alkyl, aryl, or alkylalkyl), nitro, cyano, carboxy, unsubstituted amide (i.e. —$CONH_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted and may be either unprotected, or protected as necessary, as known to those skilled in the art.

As used herein, the term 'optionally substituted alkyl' refers to the alkyl group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) optionally substituted with one or two groups independently selected from alkyl, hydroxyl, alkoxy, alkylsulfonyl, halo, or —CONRR' where R and R' are as defined above.

As used herein, the term 'optionally substituted cycloalkyl group' refers to the cyclic hydrocarbon structure where one or more hydrogen atoms can be replaced by other substituents. Cycloalkyl groups consist of a closed ring of carbon atoms, and when 'optionally substituted', it means that these hydrogen atoms within the cycloalkyl ring can be replaced with other functional groups or atoms as desired or required for a particular chemical or biochemical context. These substitutions can alter the properties and reactivity of the molecule.

As used herein, the term 'optionally substituted arylalkyl group' refers to a structural moiety in organic chemistry that combines an aryl group with an alkyl group, with the option for one or more hydrogen atoms within either or both groups to be replaced by other substituents. The aryl group is a hydrocarbon ring structure derived from benzene, characterized by its alternating single and double bonds. The alkyl group is a hydrocarbon chain structure composed of carbon and hydrogen atoms. When the term 'optionally substituted' is used, it indicates that certain hydrogen atoms within the aryl or alkyl portion of the molecule can be replaced by other functional groups or atoms.

As used herein, the term 'optionally substituted aryl group' refers to the chemical structure consisting of a ring of carbon atoms, typically derived from benzene, with the option for one or more hydrogen atoms on the ring to be replaced by other substituents. Aryl groups are characterized by a delocalized π-electron system resulting from alternating single and double bonds within the ring. The term 'optionally substituted' indicates that the aryl ring may have additional functional groups attached to it.

As used herein, the term 'apoptosis' refers to programmed cell death, which is a natural process in which cells undergo a series of tightly regulated biochemical events that ultimately lead to their self-destruction. This process is crucial for maintaining the balance between cell growth and cell death in multicellular organisms. Apoptosis is essential in various physiological processes, including embryonic development, tissue homeostasis, and immune system regulation. During apoptosis, cells undergo characteristic morphological changes, such as cell shrinkage, membrane blebbing, chromatin condensation, and cell fragmentation into smaller apoptotic bodies. These apoptotic bodies are then efficiently removed by phagocytic cells without triggering inflammation or damage to surrounding tissues. Apoptosis can be triggered by various internal and external signals, including cellular stress, DNA damage, developmental cues, and signals from the immune system. Dysregulation of apoptosis is implicated in numerous diseases, including cancer, autoimmune disorders, and neurodegenerative diseases. Apoptosis is a fundamental process that ensures the proper functioning and maintenance of tissues and organs in multicellular organisms.

As used herein, the term 'p53' refers to the tumor suppressor protein that acts as a key regulator of cell cycle arrest, DNA repair, and apoptosis. In response to cellular stress, such as DNA damage or oncogene activation, p53 can induce apoptosis by activating pro-apoptotic genes or repressing anti-apoptotic genes. It plays a critical role in safeguarding the genome by eliminating cells with irreparable DNA damage or those at risk of becoming cancerous.

As used herein, the term 'BAX' refers to the pro-apoptotic protein belonging to the BCL-2 protein family. It plays a central role in the intrinsic apoptotic pathway, which is triggered by intracellular signals such as DNA damage or cellular stress. BAX promotes apoptosis by permeabilizing the outer mitochondrial membrane, leading to the release of apoptogenic factors such as cytochrome c, which activates downstream caspases.

As used herein, the term 'Caspase 3' refers to the member of the caspase family of proteases, which are key effectors of apoptosis. It is often referred to as an executioner caspase because it cleaves multiple cellular substrates, leading to the characteristic morphological changes associated with apoptosis, including DNA fragmentation, nuclear condensation, and cytoskeletal breakdown.

As used herein, the term 'Caspase 6' refers to another member of the caspase family involved in apoptosis. Like caspase 3, it functions as an executioner caspase, cleaving specific substrates to promote the dismantling of the cell during apoptosis.

As used herein, the term 'Caspase 8' is primarily associated with the extrinsic apoptotic pathway, which is initiated by extracellular signals such as ligand binding to death receptors on the cell surface. Activation of caspase 8 leads to the subsequent activation of downstream effector caspases, ultimately resulting in cell death.

As used herein, the term 'Caspase 9' is a critical mediator of the intrinsic apoptotic pathway, which is triggered by intracellular signals such as DNA damage or mitochondrial dysfunction. Caspase 9 is activated in response to the release of cytochrome c from the mitochondria, leading to the formation of the apoptosome complex and the activation of downstream effector caspases.

As used herein, the term 'BCL-2 (B-cell lymphoma 2)' is a member of the BCL-2 protein family, which plays a crucial role in regulating apoptosis (programmed cell death). Unlike pro-apoptotic members like BAX, BCL-2 is an anti-apoptotic protein that promotes cell survival. It functions by inhibiting the release of cytochrome c from mitochondria, thereby preventing the activation of downstream caspases and blocking the intrinsic apoptotic pathway. Dysregulation of BCL-2 expression or function is implicated in various diseases, including cancer, where overexpression of BCL-2 can contribute to tumor cell survival and resistance to apoptosis.

MMP2 is a member of the matrix metalloproteinase (MMP) family, which is an enzyme involved in the breakdown of extracellular matrix components. MMP2 is particularly important for the degradation of type IV collagen, a major component of basement membranes. It plays key roles in various physiological processes, such as tissue remodeling, wound healing, and angiogenesis. Dysregulation of MMP2 activity is implicated in several pathological conditions, including cancer metastasis, where MMP2 can facilitate the invasion of tumor cells through the extracellular matrix and promote their spread to distant sites.

MMP9, also known as gelatinase B, is another MMP family member with functions similar to MMP2. MMP9 is particularly important for the degradation of gelatin, a denatured form of collagen found in the extracellular matrix. Like MMP2, MMP9 is involved in processes such as tissue remodeling, wound healing, and angiogenesis. It is also implicated in cancer progression and metastasis, where its dysregulation can promote tumor invasion and angiogenesis, facilitating the spread of cancer cells to distant sites.

COX-2 is an enzyme that plays a key role in the synthesis of prostaglandins, which are lipid compounds involved in inflammation, pain, and fever. Unlike COX-1, which is constitutively expressed in most tissues and involved in maintaining physiological functions, COX-2 is induced in response to various stimuli, including inflammatory signals, growth factors, and cytokines. Elevated levels of COX-2 are associated with inflammation and are implicated in the pathogenesis of various diseases, including arthritis, cardiovascular disease, and cancer. COX-2 inhibitors, such as nonsteroidal anti-inflammatory drugs (NSAIDs), alleviate pain and inflammation in conditions where COX-2 activity is dysregulated.

IL-6 is a pro-inflammatory cytokine produced by various cell types, including immune cells, endothelial cells, and fibroblasts, in response to infection, tissue injury, or inflammation. IL-6 plays diverse roles in immune regulation, hematopoiesis, and acute-phase responses. It can stimulate the differentiation and activation of immune cells, such as T and B cells, and regulate the production of acute-phase proteins by hepatocytes. Dysregulated IL-6 signaling is implicated in the pathogenesis of several inflammatory and autoimmune diseases and cancer. Therapeutic strategies targeting IL-6 or its receptor have shown promise in treating conditions such as rheumatoid arthritis and certain types of cancer.

IL-1β is another pro-inflammatory cytokine produced primarily by activated immune cells, such as macrophages and monocytes, in response to infection, tissue injury, or inflammatory stimuli. IL-1β plays a central role in mediating inflammation and immune responses by inducing the expression of other pro-inflammatory cytokines, promoting leukocyte recruitment and activation, and regulating fever and acute-phase protein production. Dysregulated IL-1β signaling is implicated in the pathogenesis of various inflammatory diseases, including rheumatoid arthritis, inflammatory bowel disease, and autoinflammatory syndromes. Therapeutic agents targeting IL-1β or its receptor have been developed to treat certain inflammatory conditions.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), intravaginal administration, and rectal administration. Those of ordinary skill in the art are familiar with administration techniques that can be employed with the compounds and methods described herein. In preferred embodiments, the active ingredient and/or the pharmaceutical composition described herein are administered orally.

As used herein, the term 'oral administration' refers to the most common routes of drug administration, where medications are taken by mouth and absorbed through the gastrointestinal tract. Oral medications can include tablets, capsules, syrups, or suspensions. They are convenient for patients and are often self-administered. However, oral medications may be subject to degradation in the gastrointestinal tract and may have variable absorption rates depending on factors such as gastric emptying and gastrointestinal pH.

As used herein, the term 'parenteral administration' refers to the route involving delivering medications directly into the body, bypassing the gastrointestinal tract. Parenteral administration can be achieved through various routes, including intravenous (IV), intramuscular (IM), subcutaneous (SC), or intradermal (ID) injection. These routes allow for rapid onset of action and precise control over drug delivery. Parenteral administration is often used for medications that require immediate effects, have poor oral bioavailability, or need to bypass the gastrointestinal tract due to issues such as nausea or vomiting.

As used herein, the term 'rectal administration' refers to administering medications by inserting them into the rectum using suppositories, enemas, or rectal solutions. This route is particularly useful for patients who cannot take medications orally or require local or systemic drug absorption. Rectal administration can provide rapid absorption and avoid issues associated with oral administration, such as first-pass metabolism. Common medications administered rectally include treatments for constipation, hemorrhoids, and inflammatory bowel disease.

Topical medications are applied directly to the skin or mucous membranes for localized or systemic effects. This route is commonly used for dermatological conditions, wound healing, pain management, and local anesthesia. Topical formulations include creams, ointments, gels, lotions, patches, and sprays. Topical administration allows for targeted drug delivery to specific areas while minimizing systemic side effects.

Transdermal delivery involves applying medications to the skin for systemic absorption. Unlike topical administration, transdermal medications are designed to penetrate the skin and enter the bloodstream, providing sustained drug release over an extended period. Transdermal patches are a common form of transdermal delivery and are used for medications such as hormonal contraceptives, nicotine replacement therapy, and pain management.

Intralesional administration involves injecting medications directly into a specific lesion or localized area, such as a tumor, cyst, or inflamed tissue. These injections allow for targeted delivery of medications to the site of action, minimizing systemic exposure and side effects. This route is commonly used in dermatology, oncology, and rheumatology to treat skin disorders, cancerous lesions, and joint inflammation.

Inhalation administration involves delivering medications directly into the respiratory tract for local or systemic effects. This route can be achieved through various devices such as metered-dose inhalers, dry powder inhalers, nebulizers, or vaporizers. It is commonly used for treating respiratory conditions such as asthma, chronic obstructive pulmonary disease (COPD), and respiratory infections. Inhalation allows for rapid absorption of medications into the lungs and bloodstream, resulting in quick onset of action and reduced systemic side effects.

Unless otherwise noted, the present disclosure will include all isotopes of the samples used herein.

Aspects of the present disclosure are directed toward the treatment of a cancer with N,N'-(Diselanediylbis(4,1-phenylene))bis(1-(4-(4-ethoxyphenoxy)phenyl)methanimine) (YS9). YS9 may act as an apoptotic inducer by upregulating p53, BAX, aspases, BCL-2, MMP2, and MMP9 for treatment of cancer. This may make it particularly suitable for the treatment of non-small cell lung cancer. A method of treating cancer in a subject in need thereof is described.

The method includes administering to the subject a therapeutically effective amount of the compound of Formula (I) or a pharmaceutically acceptable salt thereof:

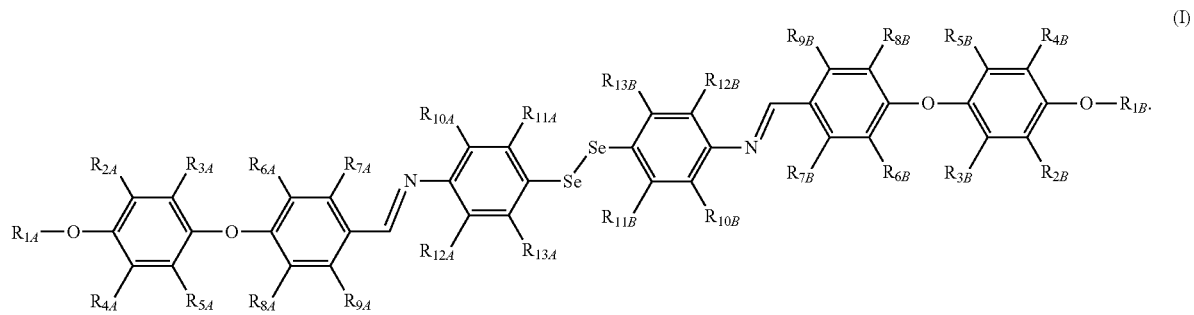

In Formula (I), each of $R_{1A}$-$R_{13A}$ and $R_{1B}$-$R_{13B}$ is independently selected from the group consisting of a hydrogen atom, a halogen atom, a nitro group, a cyano group, a hydroxyl group, an alkoxy group, an optionally substituted alkyl group, an optionally substituted cycloalkyl group, an optionally substituted arylalkyl group, and an optionally substituted aryl group. In a preferred embodiment, $R_{1A}$ and $R_{1B}$ are an alkyl group, preferably an ethyl group, and each of $R_{2A}$-$R_{13A}$ and $R_{2B}$-$R_{13B}$ is independently hydrogen. In some embodiments, the compound of formula (I) is compound (II) or a pharmaceutically acceptable salt thereof:

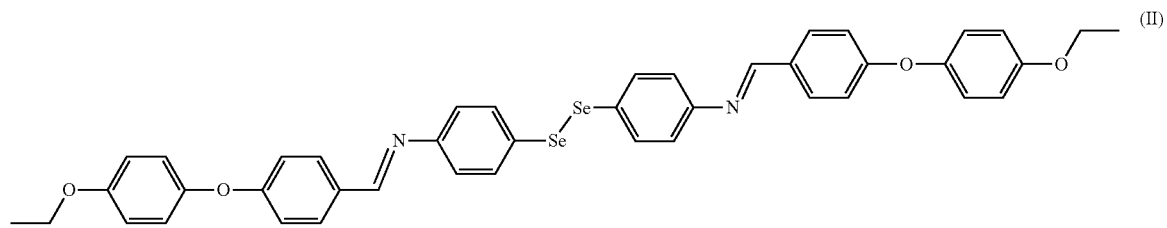 [SMILES: CCOc1ccc(Oc2ccc(/C=N/c3ccc([Se][Se]c4ccc(/N=C/c5ccc(Oc6ccc(OCC)cc6)cc5)cc4)cc3)cc2)cc1]

In some embodiments, the compound of Formula (I) or Formula (II) or pharmaceutically acceptable salt thereof acts to induce apoptosis by upregulating at least one gene selected from p53, BAX, Caspase 3, Caspase 6, Caspase 8, and Caspase 9.

In some embodiments, the compound of Formula (I) or Formula (II) or pharmaceutically acceptable salt thereof induces apoptosis by downregulating at least one gene selected from BCL-2, MMP2, and MMP9.

In some embodiments, the compound of Formula (I) or Formula (II) or pharmaceutically acceptable salt thereof acts to downregulate at least one anti-inflammatory marker gene selected from COX-2, IL-6, and IL-10. An anti-inflammatory marker gene refers to a specific gene whose expression or activity is associated with suppressing or modulating inflammatory responses within biological systems. These genes encode proteins or molecules that counteract pro-inflammatory signals, thereby promoting a state of reduced inflammation or homeostasis.

Another aspect of the present disclosure is directed to a pharmaceutical composition, including a compound of Formula (I) or a pharmaceutically acceptable salt thereof and a pharmaceutically acceptable carrier and/or excipient. In some embodiments, the compound of Formula (I) is a compound of Formula (II).

In some embodiments, the compound of formula (I) or formula (II) or a pharmaceutically acceptable salt thereof is administered as a pharmaceutical composition including the compound of formula (I) or formula (II) or a pharmaceutically acceptable salt thereof and a pharmaceutically acceptable carrier and/or excipient.

In certain embodiments, the compound of formula (I) or formula (II) of the present disclosure or a pharmaceutical composition thereof may be used in combination with one or more other antineoplastic or chemotherapeutic agents. A non-limiting list of examples of chemotherapeutic agents are aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosamide, irinotecan, lomustine, mechclorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cis-platin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguaniue), tipifarnib. Examples for antineoplastic agents which are protein kinase inhibitors include imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Examples for antineoplastic agents which are antibodies comprise trastuzumab, cetuximab, panitumumab, rituximab, bevacizumab, mapatumumab, conatumumab, lexatumumab and the like.

In some embodiments, the composition is formulated for at least one mode of administration, which is selected from oral administration, parenteral administration, rectal administration, topical administration, transdermal administration, intralesional administration, and inhalation administration.

Depending on the intended mode of administration, the composition can be in the form of solid, semi-solid, or liquid dosage forms, such as, for example, tablets, suppositories, pills, capsules, powders, liquids, or suspensions, preferably in a unit dosage form suitable for single administration of a precise dosage. The compositions will include a therapeutically effective amount of one or more of the compounds of formula (I) or formula (II) described herein or derivatives thereof in combination with a pharmaceutically acceptable carrier and, in addition, may include other medicinal agents, pharmaceutical agents, carriers, diluents or other non-active ingredients. By pharmaceutically acceptable, it meant a material that is not biologically or otherwise undesirable, which can be administered to an individual along with the selected compound without causing significant unacceptable biological effects or interacting in a deleterious manner with the other components of the pharmaceutical composition in which it is contained.

Solid dosage forms for oral administration can include capsules, tablets, pills, powders, and granules. In such solid dosage forms, the compounds of this disclosure are ordinarily combined with one or more adjuvants appropriate to the indicated route of administration. If administered a contemplated steroid or an analogue or derivative thereof can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the active compound in hydroxypropyl methylcellulose. In the case of capsules, tablets, and pills, the dosage forms can also include buffering agents such as sodium citrate, magnesium or calcium carbonate, or bicarbonate. Tablets and pills can additionally be prepared with enteric coatings.

Liquid dosage forms for oral administration can include pharmaceutically acceptable emulsions, suspensions, syrups, and elixirs containing inert diluents commonly used in the art, such as water. Such pharmaceutical compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. These solutions and suspensions can be prepared from sterile powders or granules with one or more of the carriers or diluents mentioned for use in the formulations for oral administration. A contemplated steroid or an analogue or derivative thereof of the present disclosure can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable dispersion or suspension in a non-toxic parenterally acceptable diluent or solvent, for example, in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug. Such suppositories may be advantageous for treating colorectal cancer, but may be unsuitable for treating other cancers.

Intravaginal administration may be advantageous for treating cervical cancer, but may be unsuitable for treating other cancers.

Administration by inhalation may be advantageous for treating lung cancer, but may be unsuitable for treating other cancers.

In other embodiments, the pharmaceutical composition comprising the medicinal nanocomposite disclosed herein thereof has different release rates categorized as immediate release and controlled- or sustained-release.

The amount of compound of formula (I) or formula (II) that can be combined with the carrier materials to produce a single dosage form varies depending upon the mammalian subject treated and the particular mode of administration. As used herein, the term carrier materials refers to the substances or matrices used to deliver, stabilize, or facilitate the administration of active substances, such as drugs or biological molecules, to their intended target in biological systems. The materials serve as vehicles or platforms that protect the active substance, enhance its absorption or bioavailability, and ensure controlled release or sustained delivery. Examples of carrier materials include liposomes such as doxil (liposomal doxorubicin), amBisome (liposomal amphotericin B); nanoparticles such as Abraxane; polymers such as PLGA (poly(lactic-co-glycolic acid)), Hydroxypropyl methylcellulose (HPMC); and excipients such as fillers and binders such as lactose, microcrystalline cellulose; disintegrants such as croscarmellose sodium, crospovidone.

In some embodiments, the pharmaceutically acceptable carrier and/or excipient is at least one selected from the group consisting of a buffer, an inorganic salt, a synthetic fatty acid, a vegetable oil, a fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), C12-C16 fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethyl—ammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

In some embodiments, the pharmaceutical composition further includes one or more of a sweetener, a flavoring, and a colorant. In some embodiments, the sweetener may include sucrose or aspartame. In some embodiments, the flavorant may include peppermint oil or vanilla extract. In some embodiments, the colorant may include iron oxide or titanium dioxide.

The cancer is at least one selected from the group consisting of non-small cell lung cancer, colorectal carcinoma, prostate cancer, pharynx squamous carcinoma, triple-negative breast cancer, and cervical cancer. The cancer is non-small cell lung cancer. As used herein, the term 'non-small cell lung cancer (NSCLC)' refers to the group of lung cancers that originate from epithelial cells of the lung, excluding small cell lung cancer (SCLC). NSCLC may include adenocarcinoma, squamous cell carcinoma, large cell carcinoma.

The therapeutically effective amount of the compound of Formula (I) or Formula (II) or a pharmaceutically acceptable salt thereof is from 0.1 milligrams per kilogram of body weight of the subject (mg/kg) to 1000 mg/kg, preferably 0.25 mg/kg to 975 mg/kg, preferably 0.5 mg/kg to 950 mg/kg, preferably 0.75 mg/kg to 925 mg/kg, preferably 1 mg/kg to 900 mg/kg, preferably 1.25 mg/kg to 875 mg/kg, preferably 1.5 mg/kg to 850 mg/kg, preferably 1.75 mg/kg to 825 mg/kg, preferably 2.0 to 800 mg/kg, preferably 2.25 mg/kg to 775 mg/kg, preferably 2.5 mg/kg to 750 mg/kg. In some embodiments, the therapeutically effective amount of the compound of formula (I) or formula (II), a pharmaceutically acceptable salt thereof, is from 5 mg/kg to 500 mg/kg, preferably 7.5 mg/kg to 450 mg/kg, preferably 10 mg/kg to 400 mg/kg, preferably 15 mg/kg to 350 mg/kg, preferably 20 mg/kg to 300 mg/kg, preferably 25 mg/kg to 250 mg/kg. An appropriate therapeutically effective amount may differ from one individual to another. An appropriate therapeutically effective amount in any individual case may be determined using techniques, such as a dose escalation study.

The dosage and treatment duration is dependent on factors such as the bioavailability of a drug, administration mode, toxicity of a drug, gender, age, lifestyle, body weight, the use of other drugs and dietary supplements, cancer stage, tolerance, and resistance of the body to the administered drug, etc., then determined and adjusted accordingly.

The compound of formula (I) or formula (II) or a pharmaceutical composition thereof may be administered in a single dose or multiple individual divided doses. In some embodiments, the interval of time between the administration of complex or a pharmaceutical composition thereof and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks. 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period in between. In certain embodiments, complex and one or more additional therapies are administered in less than 1 day, 1 week, 2 weeks, 3 weeks, 4 weeks, one month, 2 months, 3 months, 6 months, 1 year, 2 years, or 5 years apart.

The methods for treating cancer and other proliferative disorders described herein inhibit, remove, eradicate, reduce, regress, diminish, arrest, or stabilize a cancerous tumor, including at least one of the tumor growth, tumor cell viability, tumor cell division, and proliferation, tumor metabolism, blood flow to the tumor and metastasis of the tumor. In some embodiments, after treatment with the compound of formula (I) or formula (II) or a pharmaceutical composition thereof, the size of a tumor, whether by volume, weight, or diameter, may reduce by 5%, 10%, 15%, 20%, 25%, 30%, 40%, 50%, 60%, 70%, 75%, 80%, 85%, 90%, 95%, 99%, or 100%, relative to the tumor size before treatment. In other embodiments, after treatment with the compound of formula (I) or formula (II) or a pharmaceutical composition thereof, the tumor size may not reduce but is maintained the same as the tumor size before treatment. Methods of assessing tumor size include but are not limited to CT scan, MRI, DCE-MRI, and PET Scan.

In most embodiments of treatment, the method further comprises measuring a concentration of a biomarker and/or detecting a mutation in a biomarker before and/or after the pharmaceutical composition comprising the compound of formula (I) or formula (II) of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for breast cancer include, without limitation, BRCA1, BRCA2, HER-2, estrogen receptor, progesterone receptor, CA 15-3, CA 27.29, CEA, Ki67, cyclin D1, cyclin E, and ERβ. Potentially predictive cancer biomarkers include, without limitation, mutations in genes BRCA1 and BRCA2 for breast cancer and/or ovarian cancer, overexpression of CEA, NSE, CYFRA-21-1, CA-125, and CA-199 for lung cancer, overexpression of TYMS, mutations in genes p53 and KRAS for colon cancer. Exemplary biomarkers that may be useful to monitor or determine during a course of treatment include pro-apoptotic proteins including, p53, BAX, Caspase 3, Caspase 6, Caspase 8, Caspase 9, anti-apoptotic proteins BCL-2, MMP2, and MMP9, and anti-inflammatory markers such as COX-2, IL-6, and IL-1β.

The mutation in the biomarker may be detected by any suitable procedure known to one of ordinary skill in the art, such as restriction fragment length polymorphism (RFLP), polymerase chain reaction (PCR) assay, multiplex ligation-dependent probe amplification (MHLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, the concentration of the biomarker is measured before and after the administration. When the concentration of the biomarker is maintained, the method may further comprise increasing the effective amount of the compound of formula (I) or formula (II) by at least 5%, at least 10%, or at least 30%, up to 50%, up to 60%, or up to 80% of an initial effective amount of compound of formula (I) or formula (II) that contains in the range of 1 to 1000 mg of the anti-cancer therapeutic per kilogram of the body weight of the subject. The increased effective amount may be in a range of 10 to 900 mg/kg, preferably 15 to 800 mg/kg, more preferably 25 500 mg/kg. The subject may be administered with the increased dosage for a longer period (e.g. one more week, 2 more weeks, or 2 more months) than the duration prescribed with the initial effective amount.

In some embodiments, the mutation in the biomarker is detected before administering the pharmaceutical composition to identify subjects predisposed to the disease. For example, subjects with a BRCA1 germline mutation are at a higher risk of contracting breast cancer, or ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Numerous modifications and variations of the present disclosure are possible in light of the above teachings. It is therefore to be understood that within the scope of the appended claims, the invention may be practiced otherwise than as specifically described herein.

EXAMPLES

The following examples demonstrate a method of treating cancer in a subject in need thereof. The examples are provided solely for illustration and are not to be construed as limitations of the present disclosure, as many variations thereof are possible without departing from the spirit and scope of the present disclosure.

Example 1: Synthesis of 4-(4-ethoxyphenoxy)benzaldehyde (YS1)

Phenol (1) at 2 millimoles (mmol) was dissolved in 2 milliliters (ml) of dimethyl sulfoxide (DMSO) to prepare a first solution. Further, 4 mmol potassium carbonate and 2 mmol p-fluorobenzene were added to the first solution to obtain a mixture. The resultant mixture of the aforementioned chemicals was heated in an oil bath at 140° C. for 3 hours. After completion, the reaction was poured into ice to give a compound abbreviated as 'YS1' at an approximate yield of 67%. In other words, compound YS1 was synthesized from the reaction of 2 mmol 4-ethoxyphenol, 4 mmol potassium carbonate, and 2 mmol p-fluorobenzene. YS1 was isolated as a brown powder; at an m.p from 52° C. to 62° C., the yield is 67%. The synthetic scheme is depicted in the drawing.

Example 2: Characterization of 4-(4-ethoxyphenoxy)benzaldehyde (YS1)

Fourier transform infrared (FTIR) spectroscopy results are as follows: (v, the unit is $cm^{-1}$): 2975 $cm^{-1}$ (C—H, stretching), 1691 $cm^{-1}$ (—CHO), 1391 $cm^{-1}$, 1222 $cm^{-1}$, 1107 $cm^{-1}$.

The $^1$H-NMR spectrum was acquired at a frequency of 400 megahertz in $CDCl_3$. Observed resonances are as follows: δ 1.41-1.45 (t, 3H, $CH_3$), 2.24-2.27 (q, 2H, $CH_2$), 6.90-6.93 (d, 2H, Ar—H, J=9 Hz), 7.00-7.03 m, 4H, Ar—H, J=9 Hz), 7.79-7.83 (d, 2H, Ar—H, J=12 Hz), 9.92 (s, 1H, CHO) ppm.

The $^{13}$C-NMR spectrum was acquired at a frequency of 101 MHz in $CDCl_3$. Observed resonances are as follows: δ 190.71 (CHO), 164.11 (C, Ar—C), 156.25 (C, Ar—C), 148.03 (C, Ar—C), 131.89 (CH, Ar—C), 130.85 (C, Ar—C), 121.76 (2×CH, Ar—C), 116.75 (2×CH, Ar—C), 115.71 (2×CH, Ar—C), 63.90 (O—$CH_2$), 14.82 ($CH_3$) ppm.

MS (m/z, %): 243.30 ($M^++1$, 100). Calculated for $C_{15}H_{14}O_3$ (242.27): C, 74.36; H, 5.82; Found: C, 74.40; H, 5.87.

Example 3: Synthesis of N,N'-(Diselanediylbis(4,1-phenylene))bis(1-(4-(4-ethoxyphenoxy)phenyl) methanimine) (YS9)

1 mmol 4,4'-Diselanediyldianiline was dissolved in 5 ml of ethanol, and 1 mmol of aldehyde YS1 was added. After that, around two drops of AcOH were added to the solution, and the resultant solution was refluxed continuously for 5 hours. The formed precipitate was washed with hot ethanol and water. In other words, compound YS9 was synthesized from the reaction of 4,4'-diselanediyldianiline (1 mmol) and 4-(4-ethoxyphenoxy) benzaldehyde (2 mmol). It was isolated as a yellow powder; at an m.p. of 150° C. to 1° C., the yield was around 35%.

Example 4: Characterization of N,N'-(Diselanediyl-bis(4,1-phenylene))bis(1-(4-(4-ethoxyphenoxy)phenyl)methanimine) (YS9)

FTIR (v, $cm^{-1}$) results are as follows: 2975 $cm^{-1}$ (C—H, stretching), 1596 $cm^{-1}$ (C=N), 1100 $cm^{-1}$, 1049 $cm^{-1}$.

The $^1$H-NMR spectrum was acquired at a frequency of 400 megahertz in pyridine-$d_5$. Observed resonances are as follows: δ 8.53 (d, J=5.3 Hz, 2H), 8.09-8.02 (m, 4H), 7.89-7.84 (m, 4H), 7.59 (s, 1H), 7.39-7.30 (m, 4H), 7.18-7.14 (m, 7H), 7.10-7.02 (m, 4H), 3.96 (q, J=7.0 Hz, 4H), 1.32 (t, J=7.0 Hz, 6H).

The $^{13}$C NMR spectrum was acquired at a frequency of 101 megahertz in pyridine-$d_5$. Observed resonances are as follows: δ 161.87, 159.98, 156.22, 152.49, 148.95, 133.56, 130.97, 128.06, 122.24, 121.68, 117.27, 115.92, 63.78, 14.66.

The mass spectrum showed the following results: MS (m/z, %): 396 ($M^+$/2, 27.41), 792.10 ($M^+$, 18.23).

Elemental analysis was also performed. Calculated for $C_{42}H_{36}N_2O_4Se_2$: (792.10): C, 63.80; H, 4.59; N, 3.54; Se, 19.97. Observed: C, 93.77; H, 4.62; N, 3.57; Se, 19.94.

Example 5: Antitumor and Anti-inflammatory Activity of N,N'-(Diselanediylbis(4,1-phenylene)) bis(1-(4-(4-ethoxyphenoxy)phenyl)methanimine) (YS9)

Further, the $IC_{50}$ values of YS9 towards the most sensitive cancer cell lines (A549, PC3, FaDu, MDA-MB-468, and HeLa) were recorded to be 4.40 micrograms per milliliter (μg/mL), 11.96 μg/mL, 4.73 μg/mL, 6.00 μg/mL, and 4.00 μg/mL, respectively. These values were compared to doxorubicin as a reference drug, which showed $IC_{50}$ values of 7.63 μg/mL, 5.83 μg/mL, 13.10 μg/mL, 7.76 μg/mL, and 4.83 μg/mL against A549, PC3, FaDu, MDA-MB-468, and HeLa cancer cell lines, respectively. Furthermore, (1E,1'E)-N,N'-(diselanediylbis(4,1-phenylene))bis(1-(4-(4-ethoxyphenoxy)phenyl)methanimine) described upregulation of the pro-apoptotic proteins (p53, BAX, Caspase 3, Caspase 6, Caspase 8, Caspase 9) by 3.50, 1.95, 5.82, 10.37, 3.16, and 2.41-fold changes, respectively, compared to the control (untreated) cells. However, it showed downregulation of the anti-apoptotic proteins (BCL-2, MMP2, and MMP9) by 0.35, 0.31, and 0.48-fold changes, respectively, compared to the control (untreated) cells. Accordingly, these results confirm the potential apoptotic potential of YS9. Moreover, it showed the downregulation of the anti-inflammatory markers (COX-2, IL-6, and IL-1β) by 0.37, 0.48, and 0.46-fold changes, respectively, compared to the control (untreated) cells, which reflects a very promising anti-inflammatory-behavior-as-well.

The invention claimed is:

1. A method of treating cancer in a subject in need thereof, the method comprising administering to the subject a therapeutically effective amount of a compound of formula (I) or a pharmaceutically acceptable salt thereof:

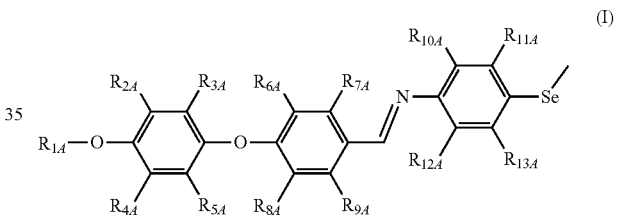

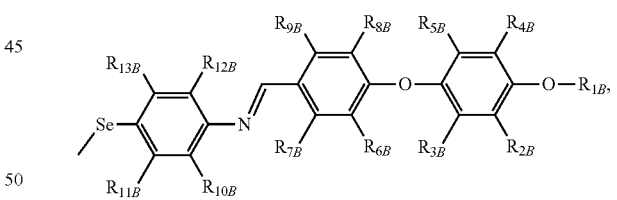

wherein each of $R_{1A}$-$R_{13A}$ and $R_{1B}$-$R_{13B}$ is independently selected from the group consisting of a hydrogen atom, a halogen atom, a nitro group, a cyano group, a hydroxyl group, an alkoxy group, an optionally substituted alkyl group, an optionally substituted cycloalkyl group, an optionally substituted arylalkyl group, and an optionally substituted aryl group, wherein the cancer is selected from the group consisting of non-small cell lung cancer, prostate cancer, pharynx squamous carcinoma, triple-negative breast cancer, and cervical cancer.

2. The method of claim 1, wherein the compound of formula (I) is compound (II) or a pharmaceutically acceptable salt thereof:

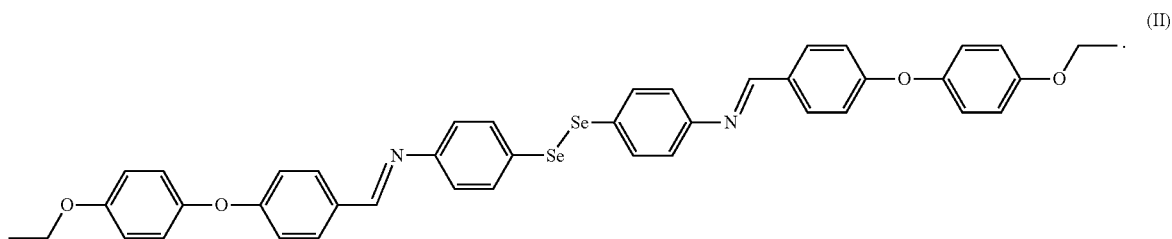 [SMILES: CCOc1ccc(Oc2ccc(/C=N/c3ccc([Se][Se]c4ccc(/N=C/c5ccc(Oc6ccc(OCC)cc6)cc5)cc4)cc3)cc2)cc1]

(II)

3. The method of claim 1, wherein the cancer is non-small cell lung cancer.

4. The method of claim 1, wherein the compound of formula (I) or pharmaceutically acceptable salt thereof acts to induce apoptosis by upregulating at least one gene selected from the group consisting of tumor suppressor protein P53 (p53), Bcl-2-associated X protein (BAX), Caspase 3, Caspase 6, Caspase 8, and Caspase 9.

5. The method of claim 1, wherein the compound of formula (I) or pharmaceutically acceptable salt thereof acts to induce apoptosis by downregulating at least one gene selected from the group consisting of B-cell lymphoma 2 (BCL-2), matrix metalloproteinase 2 (MMP2), and matrix metalloproteinase 9 (MMP9).

6. The method of claim 1, wherein the compound of formula (I) or pharmaceutically acceptable salt thereof acts to downregulate at least one anti-inflammatory marker gene selected from the group consisting of cyclooxygenase-2 (COX-2), interleukin 6 (IL-6), and interleukin 1β (IL-1β).

7. The method of claim 1, wherein the administering is by oral administration, parenteral administration, rectal administration, topical administration, transdermal administration, intralesional administration, or inhalation administration.

8. The method of claim 1, wherein the therapeutically effective amount of the compound of formula (I) or a pharmaceutically acceptable salt thereof is from 0.1 to 1000 mg/kg.

9. The method of claim 1, wherein the compound of formula (I) or a pharmaceutically acceptable salt thereof is administered as a pharmaceutical composition comprising the compound of formula (I) or a pharmaceutically acceptable salt thereof and a pharmaceutically acceptable carrier and/or excipient.

10. The method of claim 9, wherein the pharmaceutically acceptable carrier and/or excipient is at least one selected from the group consisting of a buffer, an inorganic salt, a synthetic fatty acid, a vegetable oil, a fatty ester, a surfactant, and a polymer.

11. The method of claim 10, wherein the pharmaceutical composition further comprises one or more of a sweetener, a flavoring, and a colorant.

\* \* \* \* \*